United States Patent [19]

Parry et al.

[11] 4,047,924

[45] Sept. 13, 1977

[54] REGULATING PLANT GROWTH

[75] Inventors: Keith Peter Parry, Maidenhead; Edwin Francis George, Eversley, near Basingstoke, both of England

[73] Assignee: Imperial Chemical Industries Limited, London, England

[21] Appl. No.: 634,181

[22] Filed: Nov. 21, 1975

[30] Foreign Application Priority Data

Nov. 28, 1974 United Kingdom .............. 51571/74

[51] Int. Cl.$^2$ .............................................. A01N 9/22
[52] U.S. Cl. ........................................... 71/76; 71/96
[58] Field of Search .............. 71/76, 96; 260/319.1 R

[56] References Cited

U.S. PATENT DOCUMENTS

| | | | |
|---|---|---|---|
| 2,701,251 | 2/1955 | Fox et al. | 71/96 X |
| 3,051,723 | 8/1962 | Fritz | 71/96 X |
| 3,420,838 | 1/1969 | Szmuszkovicz | 71/96 X |
| 3,671,214 | 6/1972 | Alt | 71/95 |
| 3,923,492 | 12/1975 | Collins et al. | 71/96 |

*Primary Examiner*—Joseph Paul Brust
*Attorney, Agent, or Firm*—Cushman Darby & Cushman

[57] ABSTRACT

A method of regulating the growth of, or killing, plants, which method consists essentially of applying to the plants an indole compound which is 7-chloro or 7-bromo indole, the compound being applied in an amount sufficient at least to stunt, or kill, the plants.

5 Claims, No Drawings

REGULATING PLANT GROWTH

This invention relates to a method of regulating the growth of, or killing, plants using substituted indole compounds, and to plant growth regulating and plant killing compositions containing the compounds.

U.S. Pat. No. 3,671,214 discloses that indoles substituted in the 1- and 2- positions (as well as, optionally, in other positions) have herbicidal activity. We have now discovered a small class of indoles, which are significantly more active in regulating the growth of plants.

According to the present invention, we provide a method of regulating the growth of, or killing, plants, which method consists essentially of applying to said plants an indole compound which is 7- chloro- or bromo- indole in an amount sufficient at least to stunt, or kill said plants.

The indole compounds are known chemical compounds which may be made by standard synthetic methods.

The method of the invention is applicable to retard or stunt the growth of plants, and may be used in some cases (depending on the type of plant treated, and the dose rate used) to kill plants. The method is particularly efficient in treating monocotyledonous plants (grasses). Thus, in suitable circumstances, the invention may be used selectively to control the growth of grasses, e.g. in broad-leaved crops.

Either roots or foliage of plants may be treated: the former, for example, by root drench or seed dressing, the latter, for example, by aqueous foliar spray.

The indole compounds may be used, if desired, in the form of other chemical compounds which readily react to give them under the conditions of use.

In carrying out the method, the compounds are preferably applied in the form of a composition containing a carrier suitably comprising a diluent and a surface active agent.

Solid compositions may be in the form of seed dressings, dusting powders or granules using a finely divided solid diluent, e.g. Kaolin, bentonite, keiselguhr, dolomite, calcium carbonate, talc, powdered magnesia. Fuller's earth and gypsum, or in the form of dispersible powders or grains comprising a surfactant to facilitate the dispersion of the powder or grains in liquid.

Liquid compositions include solutions, dispersions or emulsions containing surface-active agent(s) such as wetting agents, dispersing agents, emulsifying agents, or suspending agents, which may be of the cationic, anionic or non-ionic type. Suitable cationic agents are quaternary ammonium compounds, for example cetyltrimethylammonium bromide. Suitable anionic agents are soaps; salts of aliphatic monoesters of sulphuric acid, for example sodium lauryl sulphate; and salts of sulphonated aromatic compounds, for example sodium dodecylbenzenesulphonate, sodium, calcium, and ammonium lignosulphonate, butylnaphthalene sulphonate, and a mixture of sodium diisopropyl- and triisopropylnaphthalene sulphonates. Suitable nonionic agents are the condensation products of ethylene oxide with fatty alcohols such as oleyl alcohol and cetyl alcohol, or with alkyl phenols such as octylphenol, nonylphenol and octylcresol. Other non-ionic agents are the partial esters derived from long chain fatty acids and hexitol anhydrides, for example sorbitan monolaurate; the condensation product of the said partial esters with ethylene oxide; and the lecithins. Suitable suspending agents are hydrophilic colloids, for example polyvinylpyrrolidone and sodium carboxymethylcellulose, and the vegetable gums, for example gum acacia and gum tragacanth.

The aqueous solutions, dispersions or emulsions may be prepared by dissolving the active ingredient in water or an organic solvent optionally containing wetting, dispersing or emulsifying agent(s) and then, when organic solvents are used, adding the mixture so obtained to water optionally containing wetting, dispersing or emulsifying agent(s). Suitable organic solvents are ethylene dichloride, isopropyl alcohol, propylene glycol, diacetone alcohol, toluene, kerosene, methylnaphthalene, the xylenes and trichloroethylene.

The indoles may also be formulated by microencapsulation. Microcapsules may be prepared by co-acervation; or, more preferably, by stirred interfacial polymerisation of an isocyanate/diamine system. The resulting microcapsules may be used as an aqueous suspension.

The compositions for use as aqueous solutions, dispersions or emulsions are generally supplied in the form of a concentrate containing a high proportion of the active ingredient, and the concentrate is then diluted with water before use. These concentrates should usually withstand storage for prolonged periods and, after such storage, be capable of dilution with water in order to form aqueous preparations which remain homogeneous for a sufficient time to enable them to be applied by conventional spray equipment. The concentrates suitably contain 10–60% by weight of the active ingredient(s). Dilute preparations ready for use may contain varying amounts of the active ingredient(s), depending upon the desired purpose; a suitable amount is 0.01 to 10%, preferably 0.01 to 1%, by weight of active ingredient(s).

The compositions can contain other plant growth regulating agents, e.g. maleic hydrazide, 2-chloroethyltrimethylammonium chloride, chlorflurecol, $(CH_3)_2N.NH.CO.CH_2.CH_2COOH$ ('Alar') and carbetamide. These other agents may also be herbicides, e.g. simazine or atrazine, particularly those effective against broad leaved weeds, and especially those which are selectively active against broad-leaved weeds, for example hormone herbicides such as 2,4-D, MCPA, mecoprop and dichlorprop. The compositions of the invention may be formulated as mixtures with solid or liquid fertilisers, or with ferrous sulphate.

The plant growth regulating effect in the method of the invention manifested chiefly as a stunting or dwarfing is useful, for example, in stunting the growth of sugar cane thereby increasing the concentration of sugar in the cane at harvest. Grass may be treated to slow down growth, so that it need not be mown so often. Flowering of grasses, in some circumstances, may be inhibited.

The amount of indole compound applied to regulate the growth of plants will depend upon a number of factors, for example the particular formulation selected for use, whether the compound is to be applied for foliage or root uptake, the effect desired, and the identity of the plant concerned. However, in general there is used an application rate of 0.5 to 20, especially 1 to 3, kg per hectare when 7-chloro- or bromo- indole is used, and a rate of 1 to 20, especially 2 to 5 kg, per hectare for the other indole compounds. Where herbicidal effects are desired, rates used are naturally in general higher than where growth stunting is the object. In all cases routine tests are necessary to determine the best rate of application of the specific formulation for any specific purpose.

The invention is illustrated by the following Examples, in which, unless otherwise stated, parts are by weight and degrees are centigrade. Examples 1 and 2 illustrate the compositions of the invention. Examples 3 and 4 illustrate the method of the invention.

EXAMPLE 1

This Example illustrates a composition in the form of an emulsifiable concentrate formulation of 7-chloroindole, suitable for dilution with water.

|  | Weight % |
|---|---|
| 7-Chloroindole | 20 |
| Condensate of 2 moles ethylene oxide with a mixture of oleyl and cetyl alcohols | 5 |
| Mixture of calcium dodecyl benzene sulphonate with ethoxylated castor oil | 5 |
| Technical grade methylcyclohexanone | 70 |
|  | 100% |

A similar composition may be made using 7-bromoindole.

EXAMPLE 2

This Example illustrates a solid composition comprising 7-bromoindole suitable for application in the form of granules

|  | Weight % |
|---|---|
| 7-Bromoindole | 3 |
| Pumice granules | 97 |
|  | 100% |

EXAMPLE 3

Seed of Italian Ryegrass (*Lolium italicum*) was sown into separate 15 cm diameter flower pots filled with a peat/sand potting compost. When the seedling grass plants, which were grown fairly densely, had grown to approximately 10 cm in height, they were cut back to a height of 4 cm, allowed to regrow to a height of 5 cm and then sprayed with indoles useful in the invention at a rate equivalent to 5 kg/ha. Each type of treatment was applied to 4 pots. A similar number of pots were retained untreated as controls. The chemical was suspended in a 0.1% aqueous solution of a condensate of 8 moles ethylene oxide with 1 mole nonyl phenol and was applied to the plants in a volume equivalent to 1000 l/ha.

15 Days after spraying, the grass in the treated and control plots were cut back to a standard height of 4 cm and the fresh weight of foliage removed was weighed.

The percentage reductions in growth obtained are shown in Table 1 below.

TABLE 1

| COMPOUND | PERCENTAGE REDUCTION IN FRESH WEIGHT |
|---|---|
| 7-chloroindole | 94 |
| 7-bromoindole | 89 |

EXAMPLE 4

In September 1974, a randomised block trial with 3 replicates was pegged out on a perennial ryegrass (*Lolium perenne*) sward in a field in the United Kingdom. Separate plots (each measuring 2m × 3m) were sprayed with aqueous suspensions of compounds useful in the invention, prepared from emulsifiable concentrate compositions described in Example 1.

28 Days after treatment, the sprayed plots were assessed visually and scored for the relative degree of grass growth in other unsprayed plots in the experiment. As the grass treated with the chemical sprays was also noticed at this time to have become a paler green than normal, the degree of discolouration was recorded. Averaged results from the three plots to which each treatment was applied are shown in Table 2.

TABLE 2

| COMPOUND | APPLICATION RATE kg/ha | RELATIVE GROWTH % | DISCOLOURATION % |
|---|---|---|---|
| 7-chloroindole | 2 | 43 | Severe |
|  | 1 | 63 | Slight |
|  | 0.5 | 90 | Slight |
| 7-Bromoindole | 2 | 70 | Substantial |
|  | 1 | 80 | Slight |
|  | 0.5 | 80 | Slight |
| Control, untreated | — | 100 | None |

Both compounds retarded the growth of the grass in the treated plots without causing it to be killed. The treated grass eventually grew away healthily and normally.

We claim:

1. A method of regulating the growth of, or killing, plants, which method consists essentially of applying to said plants an indole compound which is 7 - chloro - or bromo - indole, said compound being applied in an amount sufficient at least to stunt, or kill, said plants.

2. A method as claimed in claim 1 wherein said compound is applied for uptake by plant foliage or by plant roots.

3. A method as claimed in claim 2 wherein said compound is applied at a rate of 0.5 to 20 kilograms per hectare.

4. A method as claimed in claim 3 wherein said compound is applied at a rate of 1 to 3 kilograms per hectare.

5. A method as claimed in claim 1 wherein said compound is applied to sugar cane in an amount sufficient to stunt the growth thereof.

* * * * *